United States Patent
Sörnmo et al.

[11] Patent Number: 6,035,231
[45] Date of Patent: Mar. 7, 2000

[54] ELECTROCARDIOGRAM SIGNAL PROCESSING APPARATUS

[75] Inventors: Leif Sörnmo; Martin Stridh, both of Lund; Lena Lundström, Stockholm, all of Sweden

[73] Assignee: Siemens Elema AB, Solna, Sweden

[21] Appl. No.: 09/176,257

[22] Filed: Oct. 21, 1998

[30] Foreign Application Priority Data

Oct. 29, 1997 [SE] Sweden .................................. 9703948

[51] Int. Cl.[7] .......................................................... A61B 5/04
[52] U.S. Cl. ................................................................ 600/509
[58] Field of Search ............................... 600/509, 510, 600/512, 516, 517, 521

[56] References Cited

U.S. PATENT DOCUMENTS

| | | |
|---|---|---|
| 3,832,994 | 9/1974 | Bicher et al. . |
| 4,721,114 | 1/1988 | DuFault et al. .......................... 600/509 |
| 4,945,917 | 8/1990 | Akselrod et al. . |
| 5,217,021 | 6/1993 | Steinhaus et al. . |

OTHER PUBLICATIONS

"Computer Detection of Atrioventricular Dissociation from Surface Electrocardiograms During Wide QRS Complex Tachycardias", Slocum et al., Circ., vol. 72 (1985) pp. 1028–1036.

*Primary Examiner*—Scott M. Getzow
*Attorney, Agent, or Firm*—Hill & Simpson

[57] ABSTRACT

A computerized apparatus for processing a multi-lead ECG beat signal to generate a residual signal has an averager unit for providing a template ventricular beat signal, and a subtraction unit for subtracting the template beat signal from the multi-lead ECG beat signal to generate the residual signal. An alignment stage is disposed before the subtraction unit and compares the template beat signal with an intermediate beat signal in the alignment parameter generator. A further subtraction unit may be provided to receive the multi-lead ECG beat signal and to subtract a signal representative of an estimated atrial signal therefrom to generate the intermediate beat signal. The alignment stage also modifies the template beat to increase the relative alignment of the two signals, with respect to at least spatial, characteristics, and emits the modified signal as an output for use by the subtraction unit as the template beat signal.

8 Claims, 3 Drawing Sheets

ELECTROCARDIOGRAM SIGNAL PROCESSING APPARATUS

BACKGROUND OF THE INVENTION

1. Field of the Invention

The present invention relates to an electrocardiogram (ECG) signal processing apparatus and in particular to an apparatus useable in conjunction with known ECG monitors to extract signals from ECG signals, for example atrial fibrillation signals, in which the effects of ventricular activity have been suppressed.

2. Description of the Prior Art

ECG technology is well established as a means for studying the function of the heart and identifying disorders of the heart. One disorder that may be studied by ECG is atrial fibrillation. It is known to facilitate the detection and characterization of atrial fibrillation in the surface ECG signal by the use of a signal, the so called "residual ECG signal," in which the ventricular activity has been first cancelled to leave the atrial signal. Such cancellation techniques have earlier been implemented by subtraction of an average QRST complex from each individual beat (J. Slocum et al. "Computer Detection of Atrioventricular Dissociation from Surface ECG During Wide QRS Complex Tachycardia" Circ., 72: 1028–1036, 1985). Due to the single lead nature of this so called "average-beat" approach, variations in the electrical axis of the heart may sometimes cause large QRS-related residuals which render the subsequent analysis of atrial fibrillation more difficult.

SUMMARY OF THE INVENTION

It is an object of the present invention to provide an electrocardiogram signaling process which avoids the aforementioned problems associated with conventional electrocardiogram signals processing systems.

The above object is achieved in accordance with the principles of the present invention in an apparatus for processing an ECG beat signal to generate a residual signal having means for providing a template ventricular beat signal which is supplied to a unit, together with an intermediate beat signal comprising the ECG beat signal, wherein one of the template ventricular beat signal or the intermediate signal is modified so as to increase a relative alignment between the template ventricular beat signal and the intermediate beat signal with respect to at least spatial, characteristics. The modified signal from this unit is supplied a subtraction unit, wherein a difference is formed either between the template ventricular beat signal and the modified signal or between the ECG beat signal and the modified signal. This difference constitutes the aforementioned residual signal.

Similar to that apparatus which uses the "average-beat" technique, the present apparatus is configured to determine an average beat signal but then performs an alignment of the average beat signal to the ventricular activity in the observed ECG beat signal in order to reduce errors due to one or both of spatial and temporal variations that may be present in the ECG prior to QRST subtraction from that observed signal beat-by-beat.

This has an advantage that an average beat may better represent the beats recorded through the ECG leads.

The apparatus may be further configured to subtract a signal representative of an estimated fibrillation signal from the observed ECG beat signal to generate an intermediate ECG beat signal useable in one or both of the generation of the average beat signal and the alignment procedure. In this way errors due to using signals which are to some extent distortions of a "pure" ventricular beat signal may be substantially reduced, since the influence of atrial activity is reduced.

A residual ECG signal, representative of an atrial signal for example, and useable for the subsequent analysis may then be output from the apparatus.

Preferably the method to correct for spatial errors employed in the apparatus according to the present invention is based on the assumption that the leads which supply the analyzed signals are spatially related by a rotation matrix. Arranging the leads in such a relationship accounts for respiratory-induced variations of the electrical axis.

More preferably temporal alignment is implemented together with spatial alignment in the device of the present invention. As discovered by the inventors these alignments together correct for the significant sources of errors in the average beat signal. Optionally, amplitude scaling in individual leads may be additionally carried out.

Least squares estimation, for example by employing an estimator derived using methods based on those described by M. Koschatz et al. ("A Weighted Procrustes Criterion" Psychometrika Vol 56,pp 229–239, 1991 ) may be applied determine estimates of the alignment parameters as described in more detail below.

DESCRIPTION OF THE PREFERRED EMBODIMENTS

To aid the understanding of the invention reference is made throughout the following description to a patient who is exhibiting atrial fibrillation. It will be understood by those skilled in the art that the atrial fibrillation signal could be replaced by any residual signal of interest which does not primarily result from ventricular activity, without departing from the invention.

Figure 1A:
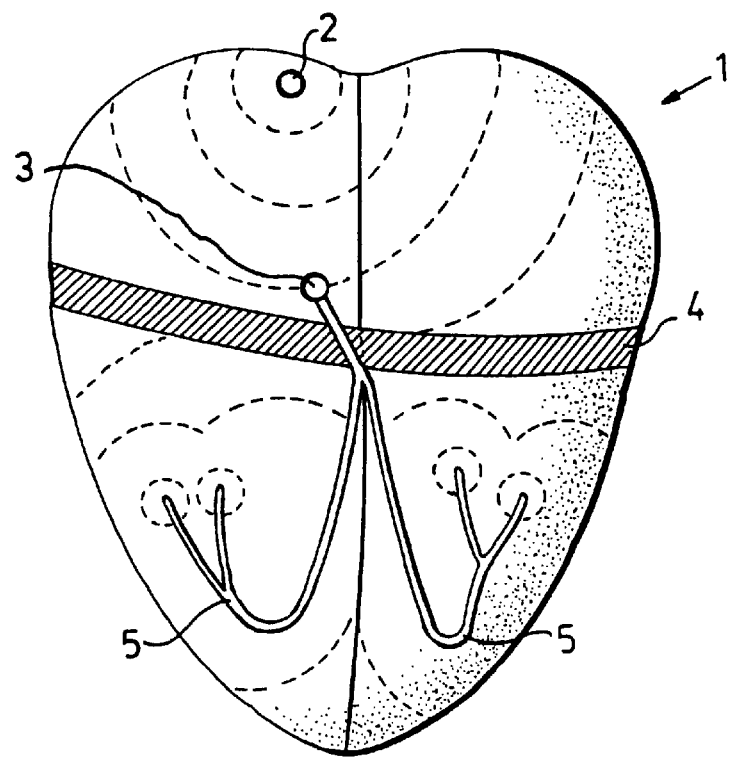
FIG. 1A schematically illustrates the conduction system of the heart.

Referring now to FIG. 1A, the heart 1 of a patient is represented as viewed from the front side. The rhythm of the heart is controlled from the sinoatrial node 2, from which an electrical signal propagates as illustrated by the dashed lines in FIG. 1A. The signal reaches the atrioventricular (AV) node 3, which acts as a collector and filter for these signals. The signals are then transferred across an electrically insulating barrier 4 by the cardiomuscular fibers 5 to the ventricles.

Figure 1B:
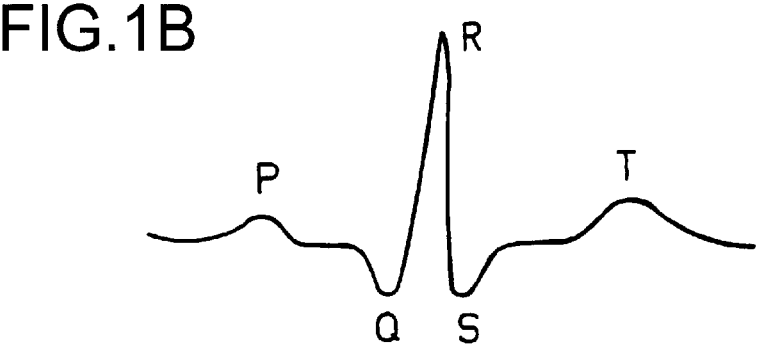
FIG. 1B shows a normal ECG trace
Figure 1C:
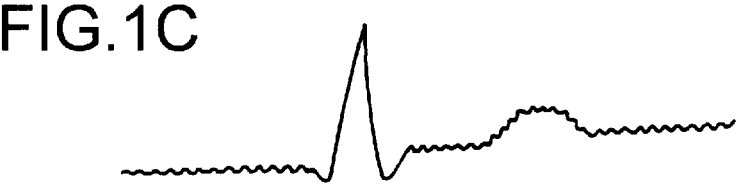
FIG. 1C shows an ECG from a patient exhibiting atrial fibrillations.

A representation of a normal ECG trace is shown in FIG. 1B, The first pulse or P-wave, P, originates from the sinoatrial node and the QRS complex and T-wave, T, originate from the ventricles. In a patient having atrial fibrillation the typical ECG trace has a fibrillation signal superimposed on the ventricular signal, the P-wave typically being absent. Such a trace is illustrated in FIG. 1C.

Figure 2:
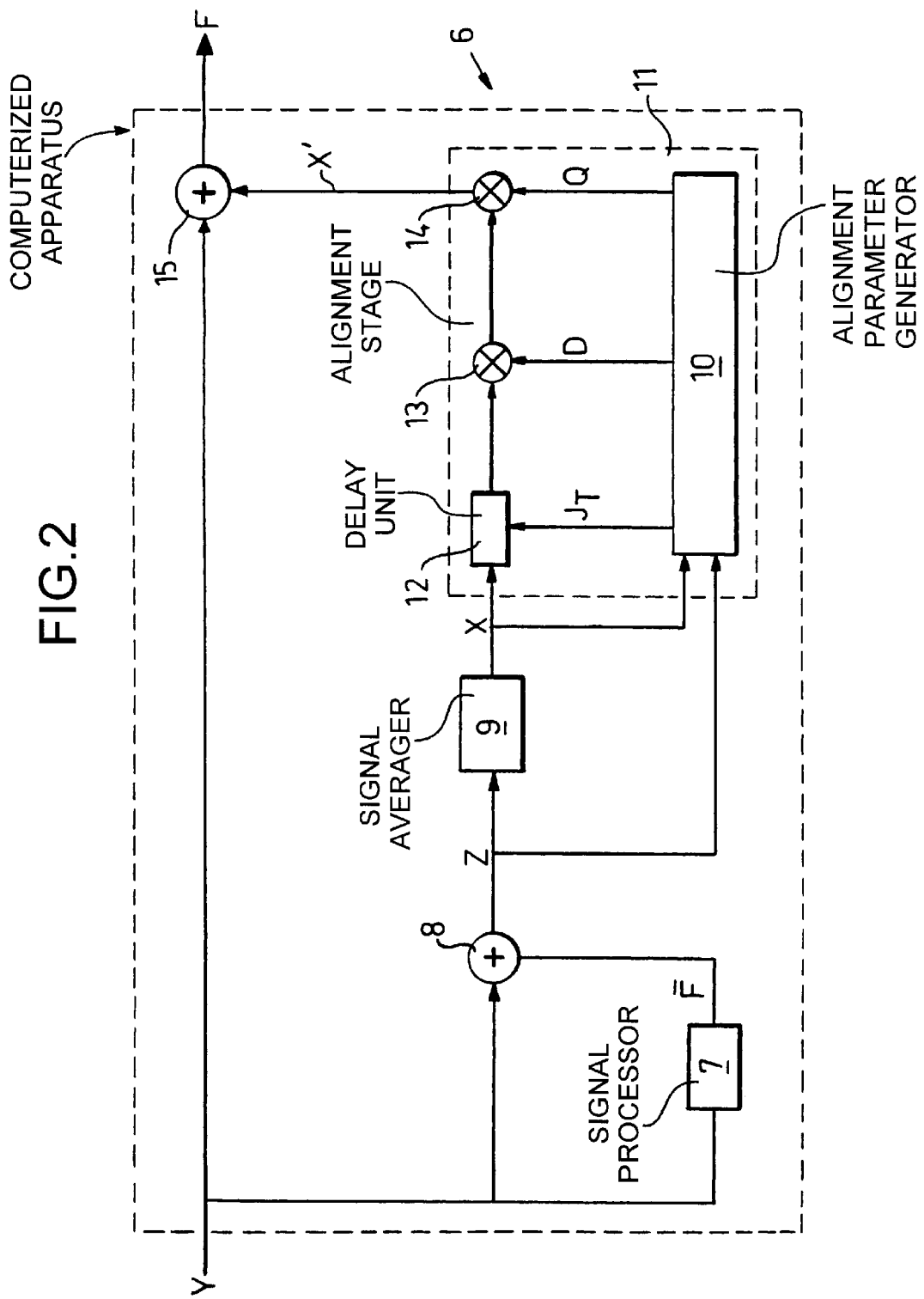
FIG. 2 is a block diagram of an embodiment of the apparatus according to the present invention.

Turning now to FIG. 2, the apparatus of the present invention, which may be implemented in a suitably programmed computer 6, is shown schematically. A digital representation of the ECG beat signal Y from a patient is supplied as an input to the computerized apparatus 6. The signal Y is passed to a signal processor 7 which analyzes the signal Y to generate an estimated atrial signal $\overline{F}$ (or residual signal). This signal $\overline{F}$ is subtracted from the original ECG beat signal Y in a subtraction unit 8 to generate an intermediate beat signal output Z, which primarily contains ventricular activity. The intermediate beat signal Z is used in a signal averager 9 to generate a template ventricular beat signal X and in an alignment parameter generator 10 of an alignment stage 11.

The generator 10 compares the two signals X and Z and calculates alignment parameters to align the two signals temporally ($J_T$), and spatially (Q and D). These parameters are then passed to, respectively, a time delay unit 12 and two signal multipliers 13 and 14, all of which operate on the template beat signal X to generate a modified template signal X' which is aligned with the intermediate beat signal Z.

Finally, the modified template signal X' is supplied to a subtraction unit 15 where it is subtracted from the ECG beat signal Y to generate an atrial signal F which may be used in the subsequent analysis of the patient's condition. Additionally the atrial signal F may be supplied back to the signal processor 7 to replace the estimated residual signal $\overline{F}$ in an iterative process to even more completely remove the ventricular beat signal from the input ECG beat signal.

It will be appreciated by those skilled in the art that the generation of the template beat signal need not be contemporaneous with the measurement of the ECG beat signal. Alternatively, the signal averager 9 may be replaced by a memory in which a representative template beat, for example obtained during a previous ECG examination of the patient, is stored for access by the generator 10 and subtraction unit 15. In this case subsequent averaging of this signal with the intermediate beat signal Z is not necessary.

It will also be appreciated that the functions of all of the components 7–15 within the computerized apparatus 6 can be implemented as suitable computer program sub-routines using standard programming techniques common in the art.

The operation of the computerized apparatus 6 is based on the assumption that one cardiac cycle of the observed ECG, Y (matrix dimension is L-by-N), with L leads and N samples, is composed of atrial fibrillation F (L-by-N), a "template" beat X (L-by-(N+2Δ)) which is influenced by a number of geometrical transformations and additive white noise W, $$Y = F + QDXJ_T + W \qquad (1)$$

The transformations that are considered are rotation, represented by the orthonormal matrix Q, and scaling by a diagonal matrix D. The time synchronization matrix $J_T$ selects those N samples from the template beat which provide the best fit to each observed beat. Strictly speaking, the atrial fibrillation is likely to be influenced by the same transformations as is X. The observation model in (1), however, is still considered since the overall effect on the fibrillation activity is considered negligible. The noise is here assumed to be uncorrelated between different leads and white within each lead (the generalization to spatially limited noise will be considered as being straightforward to those skilled in the art)

The object of the method is to produce a residual ECG which contains only atrial fibrillation. Based on the model in (1), the fibrillation signal is estimated by $$\overline{F} = Y - \overline{QDX} J_T. \qquad (2)$$

The alignment parameters Q, D and $J_T$ are chosen such that $QDXJ_T$ matches each beat as good as possible. These parameters are estimated during the QRS interval. A major problem, however, is the difficulty to perform the alignment in the presence of atrial fibrillation which influences the signal amplitude during this interval. The signal F therefore should be removed before accurate alignment can be performed. This procedure would obviously be a contradiction; to get an estimate of F, it must already be known. The solution of the inventors is to find a preliminary atrial fibrillation estimate, $\overline{F}$, which is subtracted from the observed beat, $$Z = Y - \overline{F} \qquad (3)$$

The intention with this approach is to produce an intermediate signal which is better suited for estimation of the alignment parameters.

The alignment of the template beat X to Z is done by means of a least-squares error criterion, $$\varepsilon_{min}^2 = \min_{Q, D, T} \|Z - QDXJ_T\|_F^2 \qquad (4)$$

An alternating iterative estimation algorithm is then used to calculate estimates of the alignment parameters Q, D and $J_T$. If D is known, Q can be estimated using the singular value decomposition and if Q is given, the diagonal entries in D can be obtained with a least-squares criterion. The algorithm is initialized with D=I and repeated until D and Q have converged. The time synchronization matrix is determined by evaluating the error for different values of T.

The preliminary signal estimate $\overline{F}$ is based on the fibrillation waveforms which are contained within the intervals adjacent to a QRST complex. In one implementation first, the QRST complex is blanked out from the signal. The fibrillation cycle length is then determined for every T-Q interval in the remaining signal and finally fibrillation waves from both sides in the QRST interval are copied and linearly weighted starting with one on its own side and decreasing to zero on the other. If there is not enough information to calculate the cycle length from one side, information from the other is used. In an alternative implementation, the estimated signal is generated by simply subtracting the template beat signal from the ECG beat signal.

The template beat, X, is chosen as an exponentially updated average beat that adapts to slowly changing trends in the beat morphology. It is computed from the Z signal in which $\overline{F}$ has been removed to make sure that the fibrillation will have negligible influence in the template beat.

Considering now FIGS. 3A–3D, the performance of the computerized apparatus 6 of the present invention, operating according to the above method, has been tested on ECG recordings from a number of subjects with atrial fibrillation. In this example the recordings are one hour long and sampled at 1000 Hz. Leads V1–V$_3$ (as defined according to the nomenclature common in the art) were used in the analysis.

Figure 3A:
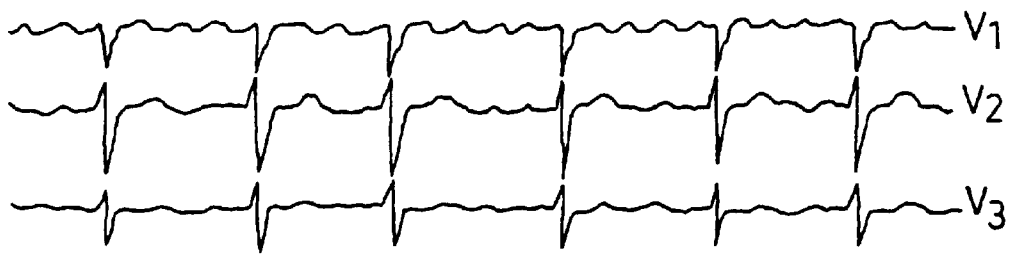
FIGS. 3A, 3B, 3C and 3D each show the same six representative beats from leads $V_1$–$V_3$ from a patient, illustrating how atrial fibrillation signals may be extracted using the apparatus of FIG. 2.
Figure 3B:
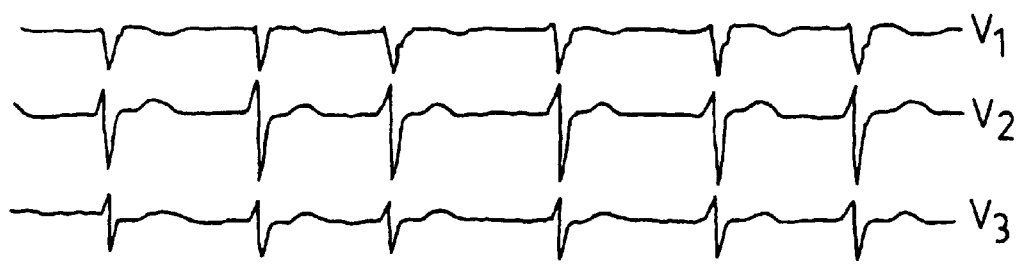
Figure 3C:
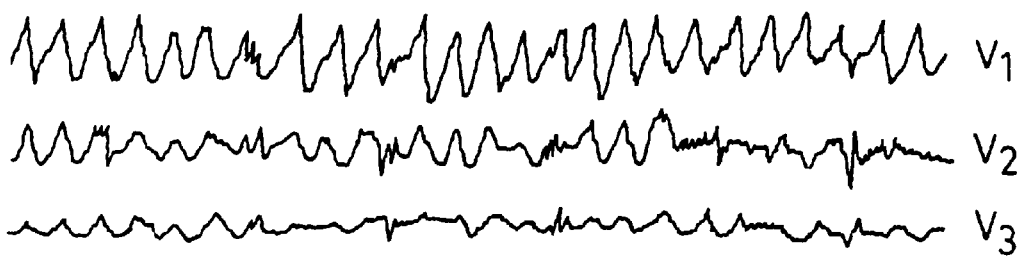
Figure 3D:
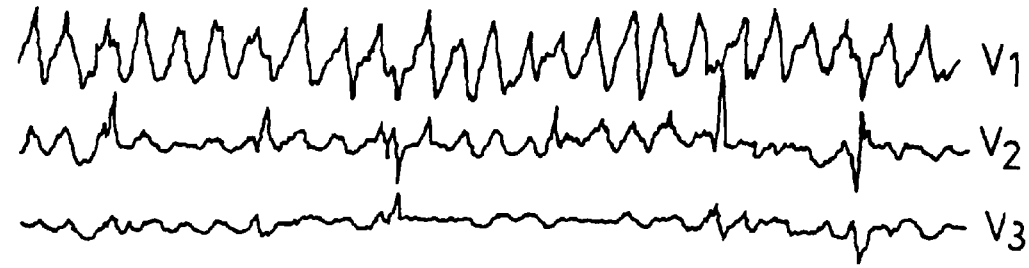

In FIG. 3A six beats from an ECG recording after baseline wander elimination is shown. FIG. 3A thus shows, for each beat, the aforementioned observed signal Y. Below, in FIG. 3B, the aligned template beats ($QDXJ_T$) are shown. This is the signal that is subtracted from those of FIG. 3A to generate the residual ECG signal. It is to be noted that there is no remaining fibrillation in this signal. The two lower figures show residual ECGs containing atrial fibrillation. In FIG. 3C the proposed method is used and in FIG. 3D average beat subtraction is used, in an apparatus operating according to the aforementioned method of J. Slocum et al.

The major difference between the results achieved with the computerized apparatus of the present 15 invention and that of the prior art can readily be observed. In FIG. 3C the spatio-temporal alignment substantially reduces undesirable residuals related to variations in the QRS complex morphology. This is evidenced by much smaller residuals related to the QRS complex in FIG. 3C than in FIG. 3D. This result is mainly due to the fact that the spatio-temporal alignment technique implemented by the present invention yields a better fit to such variations than does the apparatus employing the known average-beat subtraction method.

The computerized apparatus 6 according to the present invention is also found to be efficient in cancelling variations in QRS morphology which are to a greater or lesser extent time-synchronized, for example those variations related to respiration or body position changes. The atrial fibrillation signal generated using the apparatus of the present invention therefore should constitute a more reliable basis for further analysis of the condition of a patient's heart, for example when time-frequency analysis of atrial fibrillation is of interest.

The computerized apparatus 6 according to the present invention may be of particular value in circumstances where any such analysis is performed using an ECG monitor having leads that exhibit a poor signal-to-noise ratio, as is exemplified by the output from the leads $V_2$ and $V_3$ in FIG. 3A, where frequently occurring QRS-related residuals may hide the atrial activity of interest.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for processing a multi-lead ECG beat signal to generate a residual signal, comprising:

means for providing a template ventricular beat signal;

alignment means supplied with said template ventricular beat signal and an intermediate beat signal comprising said multi-lead ECG beat signal, for modifying one of said template ventricular beat signal and said intermediate beat signal to increase a relative alignment between said template ventricular beat signal and said intermediate beat signal with respect to at least spatial characteristics, said alignment means emitting a modified signal dependent on the comparison; and subtraction means for forming a difference selected from the group consisting of a difference between said template ventricular beat signal and said modified signal and a difference between said multi-lead ECG beat signal and said modified signal, said difference comprising said residual signal.

2. An apparatus as claimed in claim 1 wherein said alignment means comprises means for modifying said template ventricular beat signal to generate said modified signal.

3. An apparatus as claimed in claim 1 wherein said alignment means comprises means for aligning said template ventricular beat signal and said multi-lead ECG beat signal with respect to spatial and temporal characteristics.

4. An apparatus as claimed in claim 1 wherein said means for providing a template ventricular beat signal comprises averager means for generating said template ventricular beat signal by averaging a stored template ventricular beat signal with a current intermediate beat signal.

5. An apparatus for processing multi-lead ECG beat signal to generate a residual signal, comprising:

means for providing a template ventricular beat signal;

alignment means for comparing said template beat signal with an intermediate beat signal and for modifying said template ventricular beat signal dependent on the comparison to increase a relative alignment between said template ventricular beat signal and said multi-lead ECG beat signal with respect to at least spatial characteristics, said alignment means emitting a modified template ventricular beat signal;

first subtraction means supplied with said multi-lead ECG beat signal and an estimated atrial signal for forming a difference between said multi-lead ECG beat signal and said estimated atrial signal, said difference comprising said intermediate beat signal; and second subtraction means for forming a difference between said modified template ventricular beat signal and said multi-lead ECG beat signal, said difference comprising said residual signal.

6. An apparatus as claimed in claim 5 comprising means for generating said estimated atrial signal using fibrillation waveforms contained within an interval adjacent to a QRST complex of said multi-lead ECG beat signal.

7. An apparatus as claimed in claim 5 wherein said alignment means comprises means for aligning said template ventricular beat signal and said multi-lead ECG beat signal with respect to spatial and temporal characteristics.

8. An apparatus as claimed in claim 5 wherein said means for providing a template ventricular beat signal comprises averager means for generating said template ventricular beat signal by averaging a stored template ventricular beat signal with a current intermediate beat signal.

* * * * *